(12) United States Patent
Deiman et al.

(10) Patent No.: US 8,298,761 B2
(45) Date of Patent: Oct. 30, 2012

(54) NUCLEIC ACID SEQUENCES THAT CAN BE USED AS PRIMERS AND PROBES IN THE AMPLIFICATION AND DETECTION OF HSV DNA AND METHOD FOR THE AMPLIFICATION AND DETECTION OF HSV DNA USING A TRANSCRIPTION BASED AMPLIFICATION

(75) Inventors: Birgit Alberta Louisa Maria Deiman, Oisterwijk (NL); Saskia Vermeer-Van Der Laar, Boxtel (NL)

(73) Assignee: Biomerieux B.V., Boxtel (NL)

( * ) Notice: Subject to any disclaimer, the term of this patent is extended or adjusted under 35 U.S.C. 154(b) by 654 days.

(21) Appl. No.: 11/791,135

(22) PCT Filed: Nov. 17, 2005

(86) PCT No.: PCT/EP2005/012457
§ 371 (c)(1),
(2), (4) Date: Apr. 21, 2008

(87) PCT Pub. No.: WO2006/053779
PCT Pub. Date: May 26, 2006

(65) Prior Publication Data
US 2008/0280284 A1 Nov. 13, 2008

(30) Foreign Application Priority Data
Nov. 18, 2004 (EP) .................................. 04078166

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................... 435/6.1; 536/23.1; 536/24.3
(58) Field of Classification Search .................. None
See application file for complete search history.

(56) References Cited

U.S. PATENT DOCUMENTS
5,846,706 A 12/1998 Greenberg et al.
(Continued)

FOREIGN PATENT DOCUMENTS
EP 0 789 081 A2 8/1997
(Continued)

OTHER PUBLICATIONS
Saijo et al. GenBank Accession No. AB070847. 2002.*
(Continued)

*Primary Examiner* — Teresa E Strzelecka
(74) *Attorney, Agent, or Firm* — Myers Bigel Sibley & Sajovec, PA

(57) ABSTRACT

The present invention is related to a pair of oligonucleotide primers for the amplification of HSV nucleic acid comprising: a) an oligonucleotide, 10-50 nucleotides in length, preferably 10-35 nucleotides in length, comprising at least a fragment of 10 nucleotides of a sequence selected from the group consisting of: 5'-ACGTTCACCAAGCTGCTGCT-3', or its complementary sequence and b) an oligonucleotide, 10-50 nucleotides in length, preferably 10-35 nucleotides in length, comprising at least a fragment of 10 nucleotides of a sequence selected from the group consisting of: 5'CCAGGGCCCTGGAGGTGCGG-3', or its complementary sequence. The invention also relates to probes, method for amplifying an HSV DNA target, method of specific ou aspecific detection of HSV type 1 and 2 and test kit to do possible the detection of HSV. The present invention is especially useful in methods for practicing nucleic acid test.

28 Claims, 6 Drawing Sheets

U.S. PATENT DOCUMENTS

Figure 1:
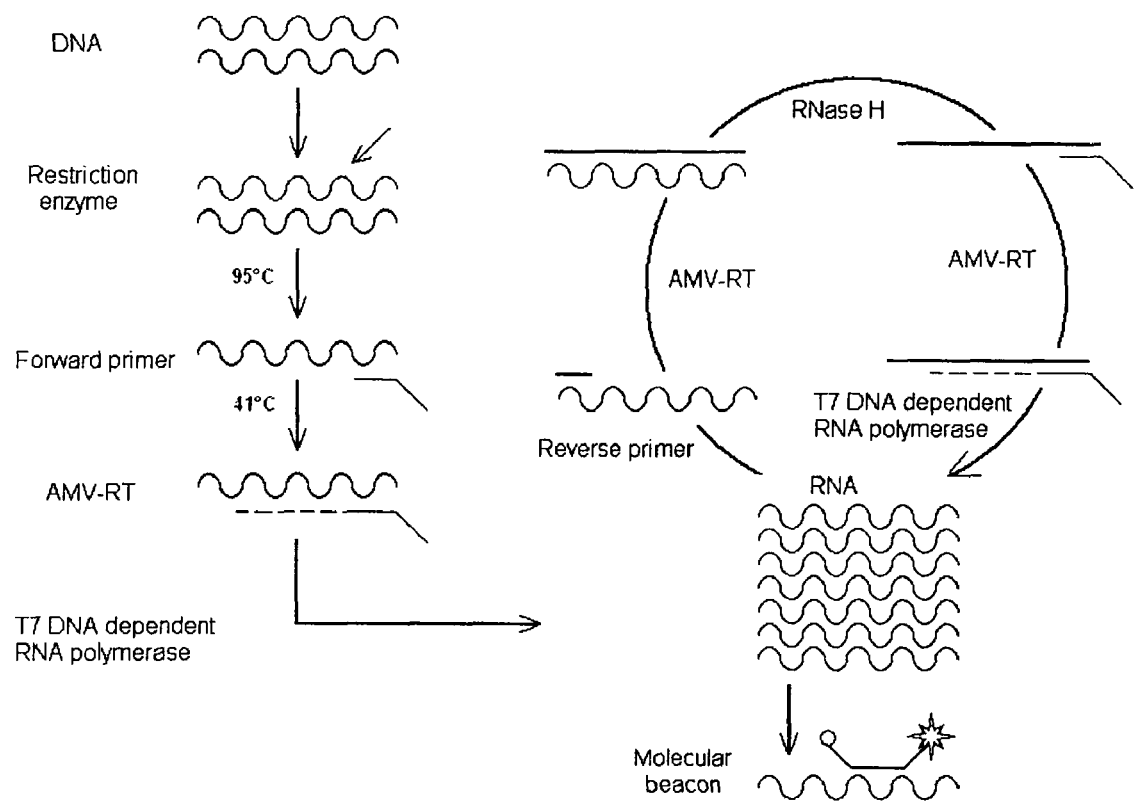

2002/0164586 A1* 11/2002 Smith et al. .................. 435/5

FOREIGN PATENT DOCUMENTS

| WO | WO 91/02091 A1 | 2/1991 |
| WO | WO 93/25707 A2 | 12/1993 |
| WO | WO 96/25909 A2 | 8/1996 |
| WO | WO 02/061390 A2 | 8/2002 |
| WO | WO 02/072881 A2 | 9/2002 |

OTHER PUBLICATIONS

Lowe et al. Nucleic Acids Research vol. 18:1757-1761. 1990.*
The stratagene Catalog. p. 39. 1988.*
Madhavan, H.N. et al., J. Clin. Virol., vol. 14, pp. 145-151 (1999).*
Kessler, H.H. et al., J. Clin. Microbiol., vol. 38, pp. 2638-2642 (2000).*
Buck, G.A. et al., Biotechniques, vol. 27, pp. 528-536 (1999).*
Kamisango, K. et al., J. Clin. Microbiol., vol. 37, pp. 310-314 (1999).*
Database accession No. A36621 "SV 1; linear; unassigned DNA; PAT; VRL; 23 BP" (1 page) (Mar. 5, 1997).
Database accession No. AAD45700 "Herpes simplex virus DNA polymerase specific probe #2" (3 pages) (Aug. 8, 2002).
Database accession No. AAD45701 "Herpes simplex virus DNA polymerase specific probe #3" (3 pages) (Aug. 8, 2002).
Database accession No. AAQ53336 "Negative primer for detection of HSV" (1 page) (Jun. 30, 1994).
Database accession No. AAT37528 "Herpes simplex virus genomic amplification primer" (1 page) (Apr. 23, 1997).
Database accession No. S68160 "Human herpesvirus 1 DNA polymerase gene, partial cds." (1 page) (Nov. 29, 1994).
International Search Report for International Application No. PCT/EP2005/012457, mailed Jun. 14, 2006 (6 pages).
Tenorio et al. "Detection and typing of human herpesviruses by multiplex polymerase chain reaction" *J. of Virological Methods* 44:261-269 (1993).

* cited by examiner

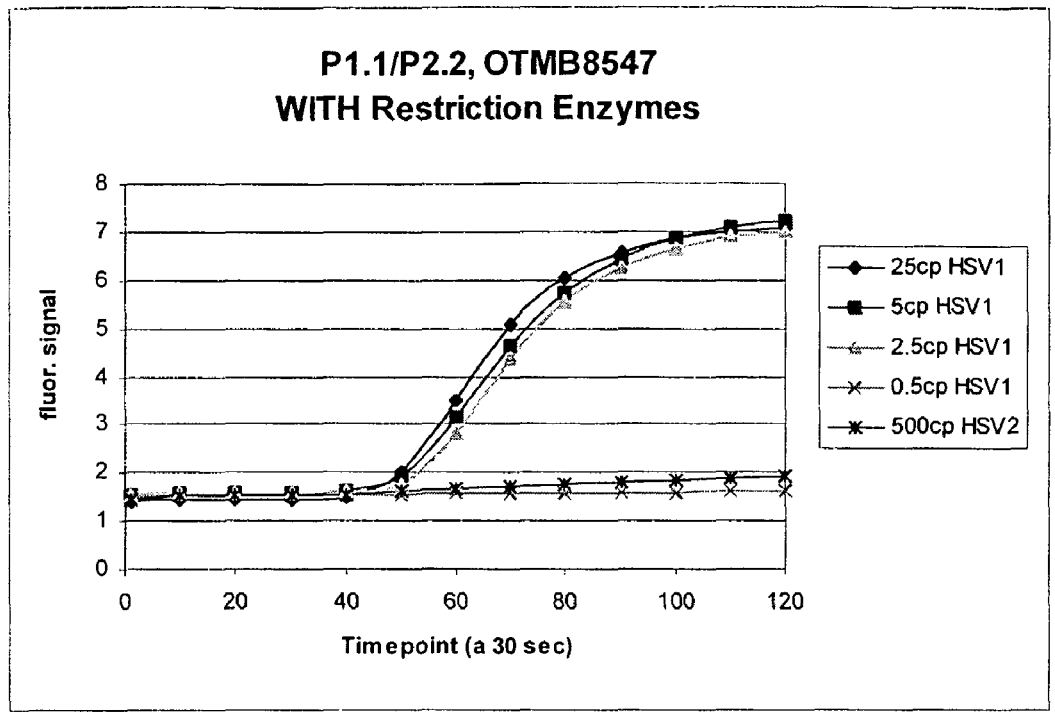
Figure 6
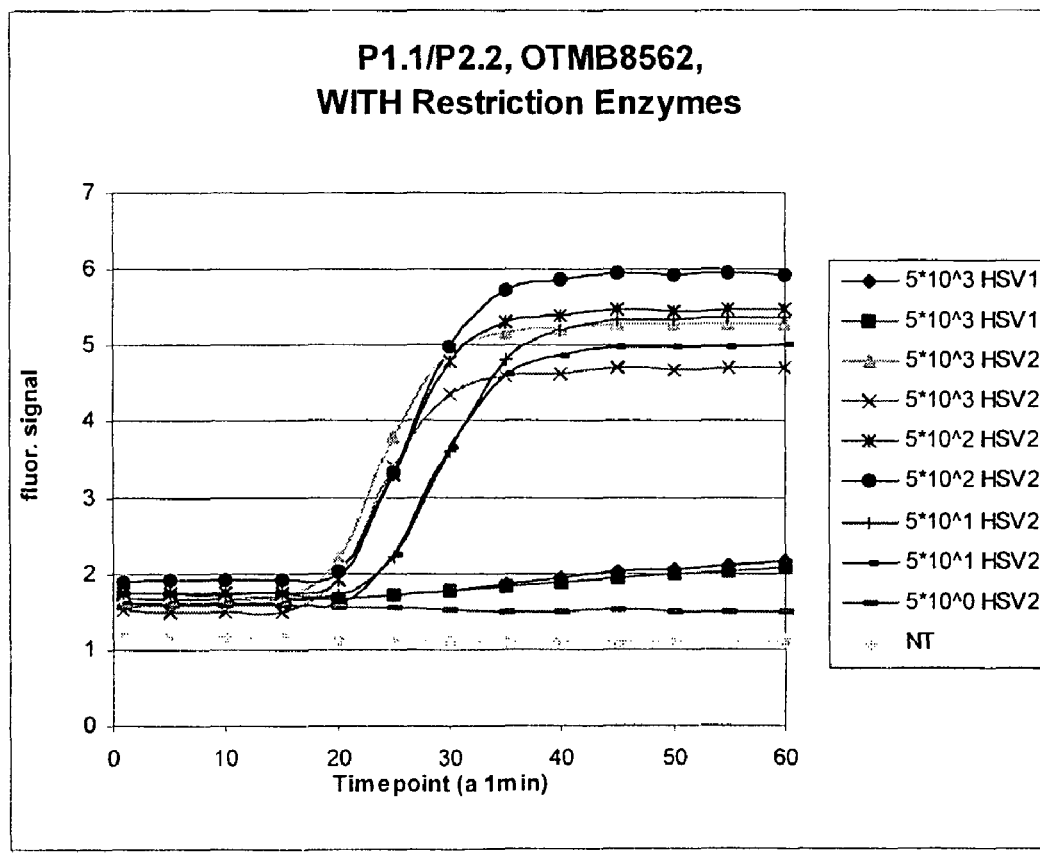

NUCLEIC ACID SEQUENCES THAT CAN BE USED AS PRIMERS AND PROBES IN THE AMPLIFICATION AND DETECTION OF HSV DNA AND METHOD FOR THE AMPLIFICATION AND DETECTION OF HSV DNA USING A TRANSCRIPTION BASED AMPLIFICATION

CROSS-REFERENCE TO RELATED APPLICATIONS

This application is a 35 U.S.C. §371 national phase application of International PCT Application Serial No. PCT/EP2005/012457 filed on Nov. 17, 2005, which claims priority to European Patent Application No. 04078166.8, filed Nov. 18, 2004, the disclosures of each of which are incorporated herein by reference in their entireties.

The present invention is related to nucleic acid sequences that can be used in the field of virus diagnostics, more specifically the diagnosis of infections with Herpes Simplex Virus (HSV). The invention is also directed to a transcription based amplification method for the amplification of DNA targets using such nucleic acid sequences.

Nucleic acid amplification methods are used in the field of molecular biology and recombinant DNA technology. These methods are used to increase the number of copies of a particular nucleic acid sequence, present in small amounts and often in an environment in which a wide variety of other nucleic acid sequences, both RNA and DNA, are also present. In particular, nucleic acid amplification methods are used to facilitate the detection or quantification of nucleic acid and are important for diagnosing for example infectious diseases, inherited diseases and various types of cancer. Nucleic acid amplification methods have also found their applications in other fields where samples are investigated in which nucleic acid may be present in minute amounts, such as forensic sciences, archeology or to establish paternity.

Several nucleic acid amplification techniques are known based on different mechanisms of action. One method for the amplification of nucleic acid is known as the "Polymerase Chain Reaction" (PCR) is described in EP-A-0.200.362 and EP-A-0.201.148 patent applications.

The present invention is also concerned with a different class of nucleic acid amplification methods namely the "transcription based amplification techniques". With these methods, multiple RNA copies are obtained from a DNA template that comprises a functional promoter recognized by the RNA polymerase. Said RNA copies are used as target from which new DNA templates are obtained etc. Gingeras et al. in WO-A-88/10315 and Burg et al. in WO-A-89/1050 have described such methods. Isothermal transcription based amplification techniques have been described by Davey et al. in EP-A-0.323.822 (relating to the NASBA method), by Gingeras et al. in EP-A-0.373.960 and by Kacian et al. in EP-A-0.408.295. Transcription based amplification reactions may also be performed with thermostable enzymes. Transcription based amplifications are usually carried out at a temperature around 41 degrees Celsius. Thermostable enzymes allow the reaction to be carried out at more elevated temperatures. Such a thermostable method is described in E-A-0.682.121 filed in the name of Toyo Boseki KK.

The methods as described in EP-A-0.323.822, EP-A-0.373.960 and EP-A-0.408.295 are isothermal continuous methods. With these methods four enzyme activities are required to achieve amplification:
an RNA dependent DNA polymerase activity,
a DNA dependent DNA polymerase activity,
an RNase (H) activity and
a DNA dependent RNA polymerase activity.

Some of these activities can be combined in one enzyme, so usually only two or three enzymes are necessary. Reverse transcriptase such as AMV (Avian Myoblastosis Virus) or MMLV (Moloney Murine Leukemia Virus) reverse transcriptase have both RNA- and DNA dependent DNA polymerase activity but also an inherent RNase H activity. In addition an RNase may be added to the reaction mixture of a transcription based amplification reaction, such as E. coli RNase H.

DNA dependent RNA polymerases synthesize multiple RNA copies from a DNA template including a promoter recognized by the RNA polymerase. Examples of RNA polymerases are polymerases from E. coli and bacteriophages T7, T3 and SP6. An example of an RNA polymerase commonly used with transcription based amplification methods is T7 polymerase. Thus the promoter that is incorporated in the template used to produce multiple copies of RNA would then be the T7-promoter. Usually the template comprising the promoter has to be created starting from the nucleic acid comprising the target sequence. Said nucleic acid may be present in the starting material that is used as input for the amplification reaction. The nucleic acid present in the starting material will usually contain the target sequence as part of a much longer sequence. Additional nucleic acid sequences may be present on both the 3'- and the 5'-end of the target sequence. The amplification reaction can be started by bringing together this nucleic acid from the starting material, the appropriate enzymes that together provide the above-mentioned activities and at least one, but usually two, oligonucleotide (s). At least one of these oligonucleotides should comprise the sequence of the DNA dependent RNA polymerase promoter.

Transcription based amplification methods are particularly useful if the input material is single stranded RNA, although single or double stranded DNA can likewise be used as input material. When a transcription based amplification method is practiced on a sample with single stranded RNA with additional sequences on both the 3'-end and the 5'-end of the target sequence a pair of oligonucleotides that is conveniently used with the methods as described in the prior art would consist of:

a first oligonucleotide (usually referred to as "promoter-primer" or "forward-primer") that is capable of hybridizing to the 3'-end of the target sequence, which oligonucleotide has the sequence of a promoter (preferably the T7 promoter) attached to its 5'-end (the hybridizing part of this oligonucleotide has the opposite polarity as the target RNA used as input material), a second oligonucleotide (usually referred to as "reverse primer") which comprises the 5'-end of the target sequence (this oligonucleotide has the same polarity as the target RNA).

When such a pair of oligonucleotides, together with all enzymes having the appropriate activities, and a sufficient supply of the necessary ribonucleotides and deoxyribonucleotides are put together in one reaction mixture and are kept under the appropriate conditions (that is, under the appropriate buffer conditions and at the appropriate temperature) for a sufficient period of time an isothermal continuous amplification reaction will start. Many variants of the above theme have been described in the prior art. A transcription based amplification reaction comprises the synthesis of single stranded RNA transcripts from a template comprising a promoter (e.g. the T7 promoter) that is recognized by an RNA polymerase (e.g. T7 RNA polymerase). A forward primer, comprising the promoter sequence, serves as a primer to initiate the synthesis of a strand of DNA complementary to the target RNA.

The primer will be extended by the activity of RNA dependent DNA polymerase. RNase H will degrade the RNA-cDNA hybrid formed. This enables the hybridization of the specific reverse primer to the cDNA. Extension of this primer by DNA dependent DNA polymerase up to the 5'-end of the cDNA results in the formation of a double-stranded promoter sequence, whereby the promoter sequence that was part of the forward primer is used as a template. This double stranded promoter will then be used by the DNA dependent RNA polymerase to produce many new RNA molecules that are complementary to the RNA target. After this initiation phase, the amplification enters a cyclic phase.

In practice, the whole sequence of events, starting from the single stranded RNA in the sample, will take place as soon as all ingredients are put together, and the mixture is brought to the appropriate temperature for the enzymes to be all active. The practitioner of the method needs not to intervene to accomplish any of these steps.

As explained above, transcription based amplification methods are particularly useful for amplifications that start from single stranded RNA. The starting material containing the nucleic acid to be amplified may not contain the target nucleic acid as RNA of a defined length. When a transcription based amplification method is performed on starting material comprising the target sequence only as double stranded DNA, either circular or linear, the DNA would have to be converted to single stranded nucleic acid. This can be achieved by separating the strands of the double stranded DNA by applying an elevated temperature (up to a 100 degrees Celsius). The first of the oligonucleotides used as primers in the amplification may than anneal to one of the single strands. The enzymes used with current transcription based amplification methods cannot withstand such a high temperature and consequently can only be added after the DNA strands have been separated. When one of the oligonucleotides anneals to a single strand DNA and is elongated, double stranded DNA is created again, and the reaction mixture would have to be subjected to an elevated temperature sufficiently high to melt the double stranded DNA into its separated strands again. Again the enzymes would be inactivated and new enzymes are to be added after the heat step has been applied. The second oligonucleotide can now be added and anneal to the strand that was created from the elongated first oligonucleotide in the first step. As one of the oligonucleotides includes a 5'-promoter sequence of a DNA dependent RNA polymerase (see above), a double stranded DNA template including a double stranded functional promoter is obtained, from which a first step of RNA production can take place. The resulting RNA transcripts may enter the cyclic phase of the amplification and the process can further be isothermal.

From the above it is evident that starting a transcription based amplification method from double stranded DNA can be a tedious process. It requires several specific actions to be taken by the practitioner; the sample has to be heated and cooled repeatedly and enzymes have to be replenished after each heating step.

Some research has already gone into the developments of transcription based amplification methods that can start from double stranded DNA, avoiding the tedious procedure described above to convert the double stranded DNA into single stranded RNA that can be used as input for the cyclic isothermal transcription based amplification.

A rather simple transcription based amplification method for dsDNA has been disclosed in WO-A-99/25868. According to the method described in this document, double stranded DNA in a sample can be amplified by means of a transcription based amplification protocol directly, without any heat treatment step (of over 90° C.) at all, or—in a preferred embodiment—with only one initial heating step. Such a double stranded DNA, which is relatively short, is to be preferred in this method. Actually, the method does not differ essentially from a conventional transcription based amplification protocol to amplify single stranded RNA.

Alternatively, the double stranded DNA in the starting material can be transcribed into RNA before the start of the amplification. Such an extra step can be based on an enzyme, for instance *E. coli* RNA polymerase, that transcribes the double stranded DNA into RNA without the presence of a promoter sequence, also referred to as a polymerase binding site. Such a process of extra steps to facilitate the amplification of double stranded DNA by transcription based amplification methods has been described in WO-A-96/02668 patent application. The extra steps described in this procedure do not only include extra handling steps and handling time, but also the use of additional ingredients, i.e. the *E. coli* RNA polymerase.

Another way of preparing suitable templates for transcription based amplification methods for double stranded DNA is described in EP-A-0.397.269. In this patent a method is described whereby double stranded DNA is pretreated with a restriction enzyme. After treatment with the restriction enzyme only one heat separation step is needed to create single stranded DNA. With this method a forward primer (promoter-primer) is used that has a 3'-part including a sequence that is complementary to the exact 3'-end of one of the single strands of DNA and a 5'-end including a promoter sequence recognized by a RNA polymerase (for example T7 RNA polymerase). When the promoter-primer is hybridized to the 3'-end of the single strand of DNA a double stranded complex is formed, of which the 5'-promoter sequence of the forward primer can serve as a template for an elongation reaction starting from the 3'-end of the DNA strand. Thus, a DNA dependent DNA polymerase forms a double stranded promoter and the resulting complex can serve as template for the DNA dependent RNA polymerase to synthesize multiple copies of RNA.

In WO-A-91/04340 also several methods are disclosed to start a transcription based amplification reaction for single stranded DNA. Again, a restriction enzyme may be used to create an appropriate 3'-end on the DNA, which can hybridize with a 3'-sequence of a promoter primer. In another embodiment of the same method, a restriction enzyme is used that cuts double stranded DNA, together with a restriction oligonucleotide that hybridizes to the target single stranded DNA and thus creates a double stranded piece of DNA that can be cut by the restriction enzyme to create the appropriate 3'-end. It is also disclosed how the defined 3'-end on the single stranded DNA may be created using a restriction enzyme that cuts single stranded DNA.

With this method a small piece of the restriction oligonucleotide will remain after the restriction enzyme has cut the double stranded complex. However, according to the disclosure of WO-A-91/04340 application, the restriction oligonucleotide is apparently chosen in such a way that after digestion, the remaining piece will be to small to stay hybridized to the 3'-end of the single stranded DNA, and thus will fall of to make room for the promoter oligonucleotide. However, the pre-treatment with a restriction enzyme as used with the prior art methods, although it may result in a sensitive transcription based assay, require many extra handling steps and handling time.

The Applicant has already filed a WO-A-02/072881 application on a transcription based amplification method including a restriction enzyme digestion. This invention provides a transcription based amplification method that enables the sensitive and specific amplification (and subsequent detection) of DNA. With the method of the invention DNA can be amplified and detected in a more efficient way than with prior art transcription based amplification methods. In contrast to the prior art methods the use of a restriction enzyme does not complicate the amplification procedure. This method for the transcription based amplification of a target nucleic acid sequence starts from DNA optionally present in a sample, and comprises the steps of:

incubating the sample in an amplification buffer with:
one or more restriction enzymes capable of cleaving the DNA at a selected restriction site, said restriction enzyme creating a defined 3'-end on one of the DNA strands,
a promoter-primer, said promoter-primer having a 5'-region comprising the sequence of a promoter recognized by a DNA-dependent RNA polymerase and a 3'-region complementary to the defined 3'-end of the DNA strand,
a second primer, having the opposite polarity of the promoter-primer and comprising the 5'-end of the target sequence, and
in case of a single stranded DNA, a restriction primer,
maintaining the thus created reaction mixture under the appropriate conditions for a sufficient amount of time for a digestion by the restriction enzyme to take place,
subjecting the sample to a heat treatment at a temperature and time sufficient to inactivate the restriction enzyme and/or to render a double stranded DNA to become single stranded,
cooling down to anneal the primers and allow the addition of enzymes,
adding the following reagents to the sample:
an enzyme having RNA dependent DNA. polymerase activity,
a enzyme having DNA dependent DNA polymerase activity
an enzyme having RNase H activity
an enzyme having RNA polymerase activity, and
maintaining the thus created reaction mixture under the appropriate conditions for a sufficient amount of time for the amplification to take place.

This method has shown an efficient way of amplifying DNA strand using a transcription based amplification method. Demonstration was given for an HBV assay, however other DNA virus could be detected/amplified using this technology, in addition to conventional amplification method such as PCR.

Thus the HSV is the virus most commonly detected in diagnostic laboratories, accounting for over 40% of the viruses that were detected in cell cultures over a 25-year period. HSV causes a variety of clinical syndromes, and anatomical sites infected include the skin, lips, oral cavity, eyes, genital tract, and central nervous system.

Generalized or disseminated HSV infection may occur in patients immunologically compromised by neoplasia, organ transplantation, inherited immunodeficiency disease, or AIDS, or through neonatal infection acquired by transmission of the virus through an infected birth canal. Most disseminated disease is fatal.

The herpesviruses comprise a large family of double stranded DNA viruses. Eight of the herpes viruses, herpes simplex virus types 1 and 2 (HSV-1 and HSV-2), varicella zoster virus (VZV), human cytomegalovirus (HCMV), Epstein-Barr virus (EBV), and human herpes viruses 6, 7 and 8 (HHV-6, HHV-7 and HHV-8), have been shown to infect humans. Several of these viruses are important human pathogens.

The two main ones are HSV-1 and HSV-2.

HSV-1 is estimated to affect 100 million people in the U.S. Primary infection of HSV-1 usually occurs between the ages of one and four. Cold sores, the visible symptom, typically appear at a later age, with 20-45% of the population over the age of fifteen affected (Whitley, Clin. Intect. Dis., 26:541-555, 1998).

Genital herpes (HSV-2) is the second most common sexually transmitted disease, with approximately 22% of the U.S. population infected with this virus (Fleming 1997).

The present invention is a methodic for evaluating a biological sample for the presence or absence of HSV by use of an amplification reaction, such as the PCR or any transcription based amplification method that could permit DNA amplification, for instance transcription based amplification method including a restriction enzyme digestion. The primers are selected from a group of potential sequences of interest one will be in one 5'-3' orientation, and the other primer will be in the inverse complement orientation. Moreother the primers will be able to amplify both HSV type 1 and HSV type 2. The exposure is under conditions in which the primers will amplify a human simplex virus-1 and/or human simplex virus-2 sequence(s) if at least one sequence is present. The sample is then examined to determine whether an amplification product exists. The presence of an amplification product indicates that the sample contains HSV.

The present invention additionally comprises exposing the amplification products to oligonucleotide probes designed to discriminate or not between the two types 1 and 2 of HSV.

Thus the invention concerns a pair of oligonucleotide primers for the amplification of Herpes Simplex Virus (HSV) nucleic acid comprising:
a) an oligonucleotide, 10-50 nucleotides in length, preferably 10-35 nucleotides in length, comprising at least a fragment of 10 nucleotides of a sequence selected from the group consisting of:
5'-ACGTTCACCAAGCTGCTGCT-3' (SEQ ID NO:1), or its complementary sequence and
b) an oligonucleotide, 10-50 nucleotides in length, preferably 10-35 nucleotides in length, comprising at least a fragment of 10 nucleotides of a sequence selected from the group consisting of:
5'-CCAGGGCCCTGGAGGTGCGG-3' (SEQ ID NO:2), or its complementary sequence.

In a particular embodiment of the pair of oligonucleotide primers, at least one of the said oligonucleotides is operably linked to a promoter nucleic acid sequence and this is true for all primer pairs diclosed in this application.

The present invention relates to a non type-specific oligonucleotide probe for the detection of HSV type 1 and/or type 2, being 10-50 nucleotides in length, preferably 10-35 nucleotides in length, and comprising at least a type-specific fragment of 10 nucleotides of a sequence consisting of:
5'-GAAAAAGTACATCGGCGTCATCT-3' (SEQ ID NO:3), or its complementary sequence.

The present invention proposes a type-specific oligonucleotide probe for the detection of HSV type 1, being 10-50 nucleotides in length, preferably being 10-35 nucleotides in length and comprising at least a type-specific fragment of 10 nucleotides of a sequence consisting of:
5'-GTCATCTACGGGGGTAAG-3' (SEQ ID NO:4), or its complementary sequence.

Furthermore, the invention covers also a type-specific oligonucleotide probe for the detection of HSV type 2, being 10-50 nucleotides in length, preferably 10-35 nucleotides in length, and comprising at least a type-specific fragment of 10 nucleotides of a sequence consisting of:

5'-GTCATCTGCGGGGGCAAG-3' (SEQ ID NO:5) , or its complementary sequence.

It is still an object of the present invention to propose a pair of type-specific oligonucleotide probes for the detection of HSV type 1 and type 2, being 10-50 nucleotides in length, preferably being 10-35 nucleotides in length, and comprising at least a type-specific fragment of 10 nucleotides of a sequence consisting of:

```
                                          (SEQ ID NO: 4)
    5'-GTCATCTACGGGGGTAAG-3' [type 1],
    and (SEQ ID NO: 5)
    5'-GTCATCTGCGGGGGCAAG-3' [type 2],
``` or their complementary sequences.

Another aim of the invention is a method for amplifying a target HSV DNA optionally present in a sample, comprising the steps of,
  incubating the sample in an amplification buffer with:
    one or more restriction enzymes capable of cleaving the HSV DNA at a selected restriction site, said restriction enzyme creating a defined 3'-end on one of the DNA strands, and
    a promoter-primer, said promoter-primer having a 5'-region comprising the sequence of a promoter recognized by a DNA-dependent RNA polymerase and a 3'-region comprising the sequence of a first primer and complementary to the defined 3'-end of the DNA strand, the first primer being 10-50 nucleotides in length, preferably 10-35 nucleotides in length, comprising at least a fragment of 10 nucleotides of a sequence selected from the group consisting of:
      5'-CCAGGGCCCTGGAGGTGCGG-3' (SEQ ID NO:2), or its complementary sequence,
    a second primer, having the opposite polarity of the promoter-primer and comprising the 5'-end of the target sequence, the second primer being 10-50 nucleotides in length, preferably 10-35 nucleotides in length, comprising at least a fragment of 10 nucleotides of a sequence selected from the group consisting of:
      5'-ACGTTCACCAAGCTGCTGCT-3' (SEQ ID NO:1), or its complementary sequence,
  maintaining the thus created reaction mixture under the appropriate conditions for a sufficient amount of time for a digestion by the restriction enzyme to take place, in presence of appropriate nucleoside triphosphates, and,
  subjecting the sample thus obtained to a heat treatment at a temperature and time sufficient to inactive the restriction enzyme(s) and/or, optionally, render at least partially the double stranded single stranded,
  adding the following reagents to the sample:
    an enzyme having RNA dependent DNA polymerase activity,
    an enzyme having DNA dependent DNA polymerase activity,
    an enzyme having RNase H activity,
    an enzyme having DNA dependent RNA polymerase activity, and
  maintaining the thus created reaction mixture under the appropriate conditions for a sufficient amount of time for the amplification to take place.

In a particular embodiment of the method, the DNA is double stranded HSV DNA.

In another particular embodiment of the method, the DNA is single stranded and the function of the promoter primer and the function of the restriction primer are combined in using a combined promoter and restriction primer comprising a sequence complementary to the region including the restriction site of the target single stranded DNA and the sequence of a promoter recognized by a DNA-dependent RNA polymerase.

Again in another particular embodiment of the method, a reverse transcriptase is used combining the activities of the enzyme having RNA dependent DNA polymerase activity and of the enzyme having DNA dependent DNA activity.

The method according to the invention proposes a reverse transcriptase that is used having inherent Rnase H activity replacing three enzymes, namely the enzyme having RNA dependent DNA polymerase activity, the enzyme having DNA dependent DNA activity as well as the enzyme having Rnase H activity.

In another particular embodiment of the method, the incubation temperature is from 35° C. to about 45° C. and preferably about 37-41° C.

In another particular embodiment of the method, the heating step is carried out at a temperature between 92° C. and 98° C. and preferably at about 95° C.

Again in another particular embodiment of the method, a restriction enzyme is used that cuts the HSV DNA at a site that is conserved among the different genotypes of HSV.

Another object of the present invention is a method for the detection of HSV nucleic acid in a sample wherein the sample is subjected to a nucleic acid amplification reaction using a pair of oligonucleotides, according to the above-described oligonucleotides, and suitable amplification reagents and the presence of any amplified nucleic acid is detected.

In a particular embodiment of this method, the detection of any amplified nucleic acid is carried out by reacting the sample with at least one oligonucleotide, according to the above-described oligonucleotides, under suitable hybridization conditions and detecting the presence of the label in any hybrids formed between the amplified sequence and the probe(s).

The amplification technique used is a transcription based amplification technique, preferably the NASBA, and the first oligonucleotide is provided with a promoter sequence recognized by a DNA dependent RNA polymerase.

The invention also proposes a method for the detection of HSV in a sample, comprising the steps of:
(a) amplifying the HSV DNA according to the method above-exposed to obtain single stranded RNA,
(b) hybridizing to the amplified RNA a non type-specific oligonucleotide probe and/or type-specific oligonucleotide probes, according to probes that are above-disclosed; and
(c) detecting hybrids formed between said RNA and said probe.

The invention concerns a specific method for the detection of HSV type 1 in a sample, comprising the steps of:
(a) amplifying the HSV DNA, according to amplification methods that are above-disclosed, to obtain single stranded RNA,
(b) hybridizing to the amplified RNA a specific oligonucleotide probe, according to the specific type 1 probe that is above-disclosed and (c) detecting hybrids formed between said RNA and said probe.

The invention concerns also another specific method for the detection of HSV type 2 in a sample, comprising the same amplification step but using a specific type 2 oligonucleotide probe, this method allowing the detection of hybrids formed between said RNA and said probe.

The present invention proposes still the use of an oligonucleotides' pair, above-described, in a nucleic acid amplification reaction or as a probe for the detection of HSV nucleic acid in a sample.

A test kit for the detection of HSV in a sample is also part of this invention. The kit comprises:
- a set of oligonucleotides above-identified,
- an oligonucleotide comprising a nucleic acid sequence substantially complementary to at least part of the amplified nucleic acid sequence, provided with a detectable label,
- suitable amplification reagents,
- optionally at least one restriction enzyme.

The invention still relates to a kit for detecting and optionally identifying HSV in a sample, wherein the kit comprises a pair of primers, wherein the first primer comprises an RNA polymerase promoter sequence and a hybridizing sequence being 10-50 nucleotides in length, and preferably being 10-35 nucleotides in length, and comprising at least a fragment of 10 nucleotides of a sequence consisting of 5'-CCAGGGC-CCTGGAGGTGCGG-3' (SEQ ID NO:2), and the second primer sequence being 10-50 nucleotides in length, and preferably being 10-35 nucleotides in length, and comprising at least a fragment of 10 nucleotides of a sequence consisting of 5'-ACGTTCACCAAGCTGCTGCT-3' (SEQ ID NO:1).

In a particular embodiment of the kit, it further comprises an oligonucleotide probe containing a nucleic acid sequence capable of hybridizing to the region of the DNA amplified using the first primer and the second primer.

Finally the invention concerns a test kit, including suitable amplification reagents for performing a transcription based amplification technique, preferably the NASBA.

The invention will now be described further, by way of examples, with reference to the accompanying drawings, in which:

FIG. 1: Schematic presentation of DNA NASBA including restriction enzyme digestion. The restriction enzyme (arrow) is only active during the initiation phase of NASBA. After digestion, the forward primer is hybridized to the template. AMV RT will extend the 3'-end of the target strand (black) of the DNA, using the forward primer, including the T7 promoter sequence (dark grey) as template. The T7 DdRp will recognize the double stranded T7 promoter sequence and RNA amplicon (light grey) production will begin. The RNA amplicon sequence is complementary to the target DNA strand. During the cyclic phase, the RNA amplicon will be amplified and detected by molecular beacon technology. RNase H and the reverse primer are only required during the cyclic phase.

Figure 2:
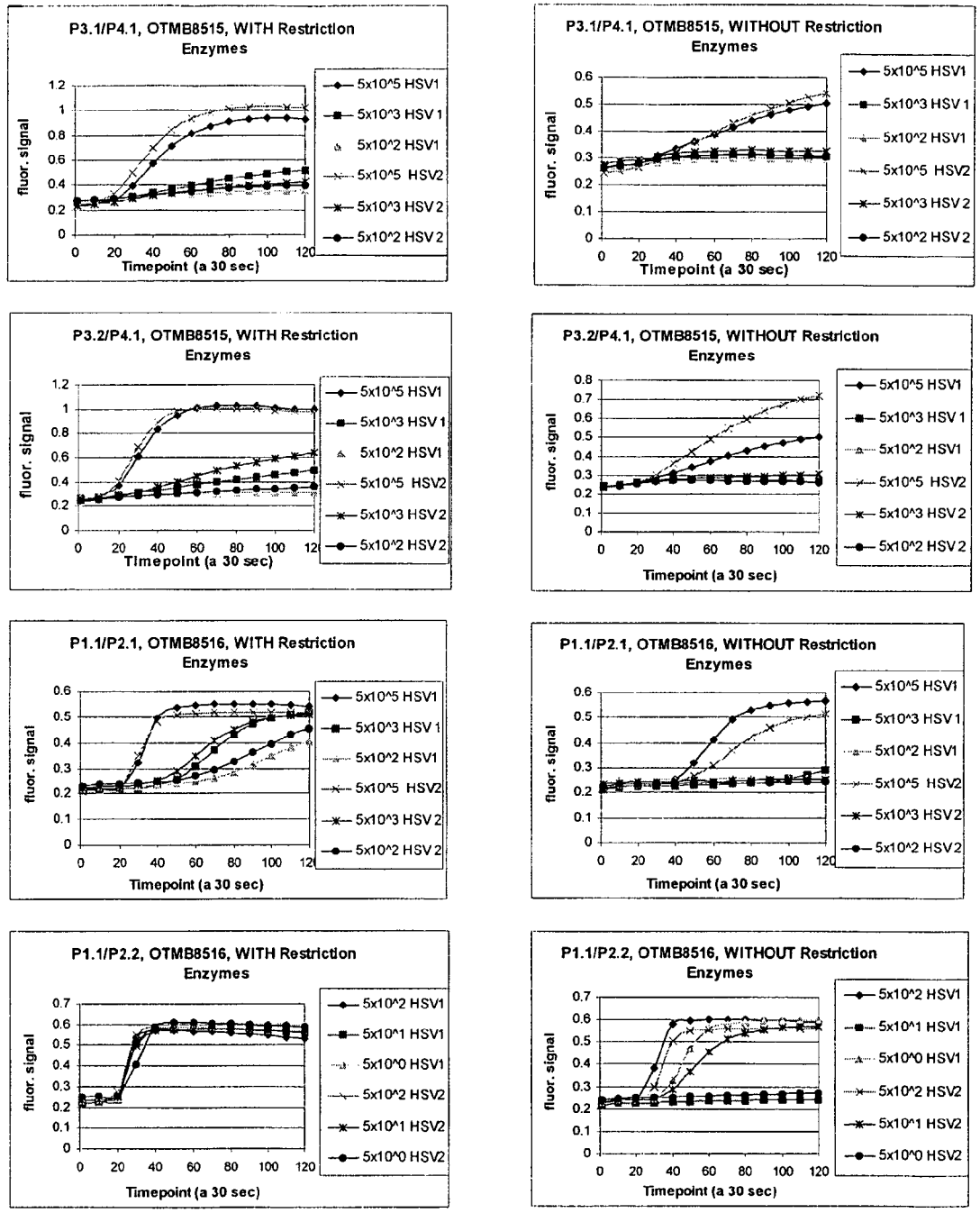

FIG. 2: Amplification of HSV DNA with different primer sets. NASBA was performed in the presence and absence of ApaI and SalI. Four different HSV POL primer sets were analyzed: P1.1/P2.1, P1.1/P2.2, P3.1/P4.1, P3.2/P4.1 (Table 1). A 10-fold dilution series of a linear DNA including part of the HSV POL region of HSV 1 or HSV 2 was used as template. The generic molecular beacons OTMB8515 and OTMB8516 were used to detect the minus strand and plus strand of both HSV type 1 and HSV type 2, respectively.

Figure 3:
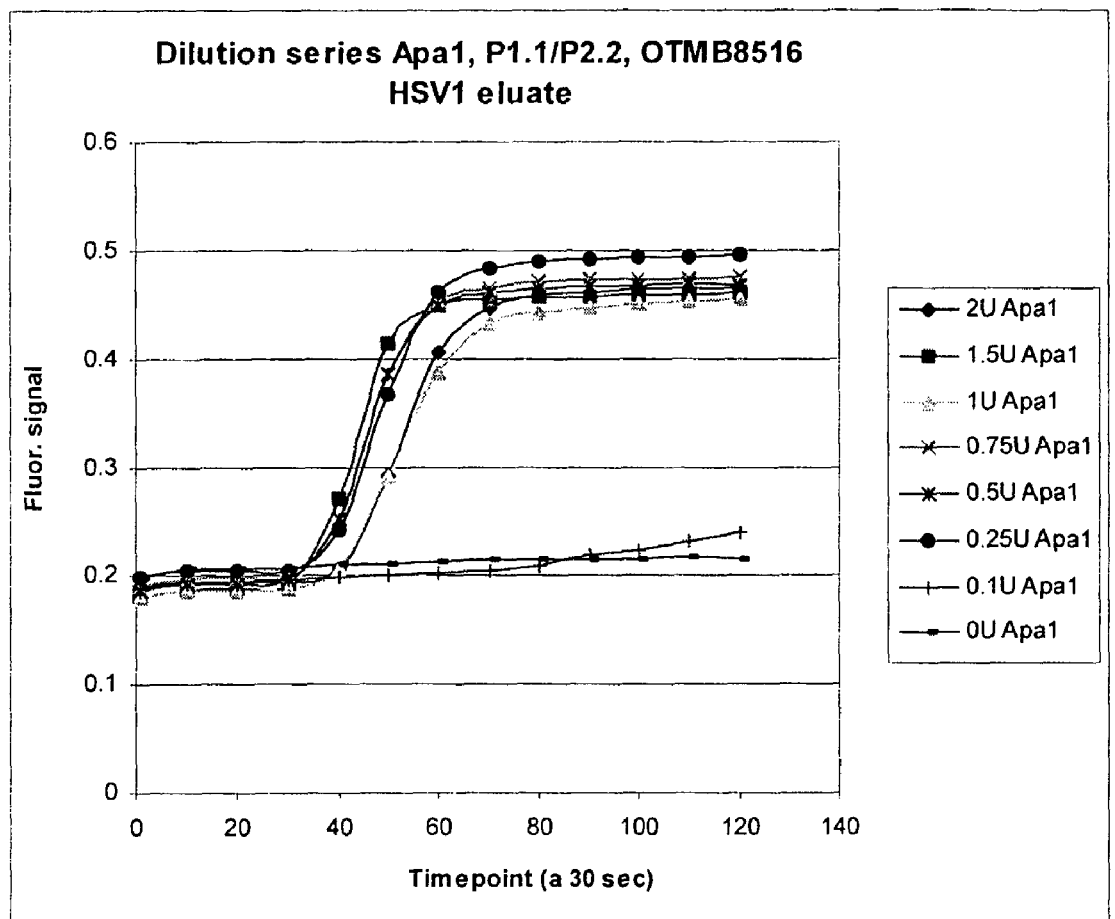

FIG. 3: Amplification of HSV DNA including Apa I digestion. A dilution series of Apa I was tested. HSV POL P1.1 is used as forward primer, P2.2 as reverse primer and OTMB8516 as molecular beacon (Table 1). A $10^5$-fold dilution of a HSV type 1 tissue culture sample (strain SC16) extract is used as template.

Figure 4:
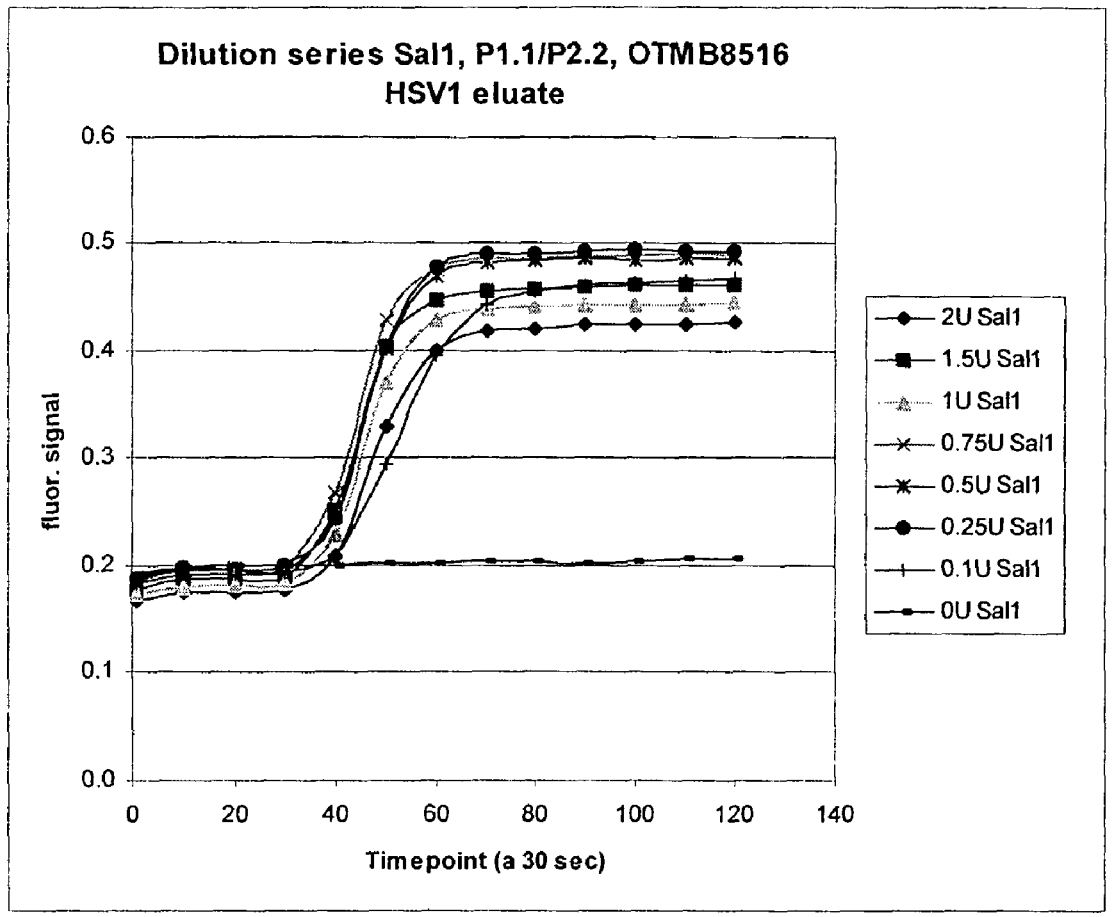

FIG. 4: Amplification of HSV DNA including SalI digestion. A dilution series of Sal I was tested. HSV POL P1.1 is used as forward primer, P2.2 as reverse primer and OTMB8516 as molecular beacon (Table 1). A $10^5$-fold dilution of a HSV type 1 tissue culture sample (strain SC16) extract is used as template.

Figure 5:
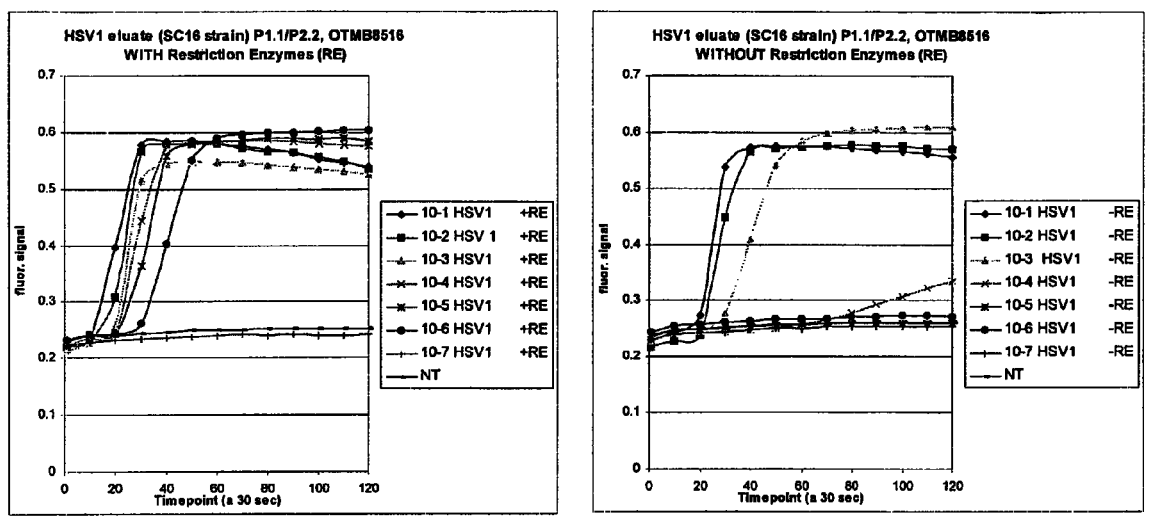

FIG. 5: Amplification of HSV type 1 tissue culture sample including Apa I and Sal I digestion. A dilution series of a HSV type 1 tissue culture sample (strain SC16) was tested in the absence and presence of the restriction enzymes Apa I and Sal I. Primer set P1.1/P2.2 and the generic beacon OTMB8516 are used (Table 1).

FIG. 6: Specific detection of HSV type1 and HSV type 2 including Apa I and Sal I digestion. For the specific detection of HSV type 1 and HSV type 2 DNA, specific molecular beacons were designed in the amplification area of the POL-gene of HSV using primer set POL P1.1/P2.2. Molecular beacon OTMB8547 is specific for HSV type 1 detection and molecular beacon OTMB8562 is specific for HSV type 2 detection. Dilution series of a linear DNA of HSV type 1 and HSV type 2 were tested.

The necessary (appropriate for an adequate amplification) nucleoside triphosphates may be present already during the incubation step with the restriction enzyme (s), for example as part of the said amplification buffer. They may, however, be added later on in the process, for example together with the enzymes after the heat treatment.

The person skilled in the art knows the enzymes used for the transcription based amplification method, and the conditions under which the transcription based amplification method is carried out and is aware of all the usual modifications that can be made with regard to optimizing transcription based amplification reactions. For example, the forward primer, the promoter primer, may comprise a purine region between the promoter sequence on the 5' end of the primer and the hybridizing sequence on the 3' end of the primer.

The sequence of the primers is largely determined by the position of the restriction site chosen.

The 3'-end of a forward primer should anneal to the target sequence directly upstream of the restriction site. The primer may vary in length as long as it is sufficiently long to hybridize under the conditions used with the amplification reaction. In general the hybridising part of the primer consists of about 10 to about 35 nucleotides.

A restriction enzyme is an enzyme that can cut double stranded DNA at a selected site (i.e. a specific nucleotide sequence recognized by the enzyme). In selecting an appropriate restriction enzyme for the method of the invention care should be taken that a restriction site is chosen that is present in all variants of the target DNA (for example, a restriction site that is present in all genotypes of a particular virus, if the amplification is carried out to detect viral DNA in the sample). The restriction site should not be present in the DNA sequence in between the primers.

The addition of the restriction enzyme results in the creation of a defined 3'-end of the target strand of the DNA, which is then available for binding to the hybridizing part of the promoter primer. An additional aspect is that, because of the digestion, denaturation of that part of the DNA will be improved and so primer binding will be facilitated.

The promoter oligonucleotide containing the T7-promoter sequence should be designed in such a way that the hybridizing part will interact with the template directly upstream of the restriction site. The enzyme having DNA dependent DNA polymerase activity (usually a reverse transcriptase such as MMLV-RT or AMV-RT) can extend the 3'-end of the target strand of the DNA created by the digestion with the restriction enzyme, using the primer as template. A double-stranded T7-promoter sequence will be formed and the production of amplicon RNA can start.

The invention will be further exemplified by the following Examples.

EXAMPLE 1

Amplification of HSV DNA

Two conserved restriction sites (ApaI and SalII) are encoded in the highly conserved POL-gene of HSV DNA. Based on these restriction enzymes, primers and molecular beacon probes were designed. HSV 1 and HSV 2 DNA was isolated from patient material, using the NucliSens Extractor (Product Reference: 200272 (220V) or 200236 (110V), BioMerieux B. V., Boxtel, The Netherlands). Following the standard procedure as described for RNA isolation (Operator Manual Extractor, 41001-9, rev A, 1999), a 50 µl extract is obtained. Five µl of the extract is used per assay. The restriction enzyme digestion was performed in NASBA buffer (40 mM Tris-HCl pH 8.5, 12 mM MgCl$_2$, 70 mM KCl, 15% v/v DMSO, 5 mM DTT, 1 mM each dNTP, 2 mM ATP, 2 mM CTP, 2 mM UTP, 1.5 mM GTP, 0.5 mM ITP, 0.2 µM primers, 0.1 µM molecular beacon probe, and 1.0 unit restriction enzyme Apa I (Product Reference: E1005Y, Amersham Biosciences, Freiburg, Germany) and 1.0 unit restriction enzyme SalI (Product Reference: E1080Y, Amersham Biosciences, Freiburg, Germany). After incubation during 15 minutes at 41° C., the restriction enzymes were heat-inactivated and the DNA template was denatured at 95° C. for 5 minutes. Hybridization of the primers occurred during cooling down to 41° C. for 3 minutes. Subsequently, NASBA enzymes (2.1 µg BSA, 0.08 units RNase H, 32 units T7 RNA polymerase and 6.4 units AMV reverse transcriptase) were added, the reaction mixture was mixed by gently tapping and short centrifugation, and the amplification and real-time detection was started. The reaction mixture was incubated at 41° C. in the NucliSens EasyQ Analyzer (Product Reference: 200276, BioMerieux B. V., Boxtel, The Netherlands) for 60 minutes with fluorescence monitoring every minute.

After restriction enzyme digestion and hybridization of the primers to the target, the forward primers, including a T7 promoter sequence (P1 and P3, table 1), are used as template by AMV RT to extend the 3'-end of the target strand at the restriction site. A double stranded T7 promoter is formed what is used by T7 for the production of amplicons that will be reused until the primers are finished (see FIG. 1).

EXAMPLE 2

Amplification of HSV DNA with Different Primer Sets

A NASBA assay was performed in the absence and presence of the restriction enzymes Apa I and Sal I. Four different HSV POL primer sets were analyzed: P1.1/P2.1, P1.1/P2.2, P3.1/P4.1, P3.2/P4.1, as depicted in Table 1.

TABLE 1

Primer and probe sequences*

| Primer/Probe | Sequence | Label |
|---|---|---|
| HSV_pol P3.1 | 5'-*AATTCTAATACGACTCACTATA* gggcc ctggtcgacctgctgttttacgac-3' (SEQ ID NO: 10) | |
| HSV_pol P3.2 | 5'-*AATTCTAATACGACTCACTATAGGGAGA* cctgctgttttacgacgataccg-3' (SEQ ID NO: 11) | |
| HSV_pol P4.1 | 5'-tctgctcagttcggcggtga-3' (SEQ ID NO: 12) | |
| HSV_pol P1.1 | 5'-*AATTCTAATACGACTCACTATAGGGAGA* ccagggccctggaggtgcgg-3' (SEQ ID NO: 13) | |
| HSV_pol P2.1 | 5' gggcgacaagatggcgagcca-3' (SEQ ID NO: 14) | |
| HSV pol P2.2 | 5' acgttcaccaagctgctgct-3' (SEQ ID NO: 2) | |
| OTMB8515 | 5'-CGATCG ccccgaacgcctgcagtcc CGATCG-3' (SEQ ID NO: 15) | FAM |
| OTMB8516 | 5'-CGATCG aaaagtacatcggcgtcatct a CGATCG-3 (SEQ ID NO: 16) | FAM |
| OTMB8547 | 5'-CT6TCCC gtcatct6cggiggtaag 777AT67-3' (SEQ ID NO: 17) | FAM |
| OTMB8562 | 5'-CGATCG gtcatctgcgggggcaag CGATCG-3' (SEQ ID NO: 18) | Cy-5 |

*The T7-promoter sequence is written in capitals and italics, the hybridizing sequence in lower case, the stem sequence of the probe in capitals and bold.
7 = Methoxy G, 6 = Methoxy A and i = inosine Inosine is included to increase specificity and methoxy G or A is useful to increase the amplicon binding (DNA/RNA) interaction.

The P1 and P3 are forward primers and P2 and P4 are reverse primers. A 10-fold dilution series of a linear DNA including part of the HSV POL region of HSV type 1 or HSV type 2 was used as template. The generic molecular beacons OTMB8515 and OTMB8516 were used to detect the minus strand and plus strand of both HSV type 1 and HSV type 2, respectively. For all primer sets, a clear improvement of the reaction kinetics was shown if restriction enzymes were included, see FIG. 2. Dependent on the primer set, a 10-1000 fold increase in sensitivity and a 5-10 minutes decrease of "time to positivity" (TTP) was obtained in the presence of restriction enzymes. Both are indications for an improved amplification reaction. The best kinetics and sensitivity was obtained with primer set P1.1/P2.2.

EXAMPLE 3

Amplification of HSV DNA Including Apa I Digestion

To optimize the amount of Apa I in the reaction, a dilution series of Apa I was tested. HSV POL P1.1 is used as forward primer, P2.2 as reverse primer and OTMB8516 as molecular beacon (see Table 1 above). A $10^5$-fold dilution of a HSV type 1 tissue culture sample (strain SC16) extract is used as template. The optimal concentration of Apa I was determined to be 0.25 units or more as deducted from FIG. 3.

EXAMPLE 4

Amplification of HSV DNA Including Sal I Digestion

To optimize the amount of Sal I in the reaction, a dilution series of Sal I was tested. HSV POL P1.1 is used as forward primer, P2.2 as reverse primer and OTMB8516 as molecular beacon (Table 1). A $10^5$-fold dilution of a HSV type 1 tissue culture sample (strain SC16) extract is used as template. The optimal concentration of Sal I was determined to be 0.1 units or more, as exposed in FIG. 4.

EXAMPLE 5

Amplification of HSV Type 1 Tissue Culture Sample (Strain SC16) Including ApaI and SalI Digestion A dilution series of a HSV type 1 tissue culture sample (strain SC16) was tested in the absence and presence of the restriction enzymes Apa I and Sal I. Primer set P1.1/P2.2 and the generic beacon OTMB8516 are used, see Table 1. In the absence of restriction enzymes a 1000-fold dilution of the virus was detectable, see FIG. 5. However, in the presence of restriction enzymes a 1000.000 fold dilution was still positive, showing that a 1000-fold increase in sensitivity was obtained. In addition a decrease of TTP of 5 minutes was observed in the presence of restriction enzymes. Both are indications for an improved amplification reaction indicating that the addition of restriction enzymes also improves amplification of tissue culture material.

EXAMPLE 6

Specific Detection of HSV Type 1 and HSV Type 2 Including Apa I and Sal I Digestion For the specific detection of HSV type 1 and HSV type 2 DNA, specific molecular beacons were designed in the amplification area of the POL-gene of HSV using primer set POL P1.1/P2.2. To discriminate between HSV type 1 and HSV type 2, specific beacons are directed against part of the amplicon in which a difference of two nucleotides exists between HSV type 1 and HSV type 2. Molecular beacon OTMB8547 is specific for HSV type 1 detection and molecular beacon OTMB8562 is specific for HSV type 2 detection. Dilution series of a linear DNA of HSV type 1 and HSV type 2 were tested. The HSV type 1 specific beacon OTMB8547 was shown to be specific for HSV1, as exposed in FIG. 6, and the specific HSV type 2 molecular beacon OTMB8562 was shown to be specific for HSV type 2.

The invention claimed is:

1. A pair of isolated oligonucleotides for the amplification of herpes simplex virus (HSV) nucleic acid consisting of:
   a) a first isolated oligonucleotide, consisting of the nucleotide sequence: 5'-ACGTTCACCAAGCTGCTGCT-3' (SEQ ID NO:1); and
   b) a second isolated oligonucleotide, being 20 nucleotides in length and comprising the nucleotide sequence: 5'-CCAGGGCCCTGGAGGTGCGG-3' (SEQ ID NO:2).

2. A pair of isolated oligonucleotides according to claim 1, wherein at least one of said first isolated oligonucleotide or second isolated oligonucleotide is operably linked to a promoter nucleic acid sequence.

3. A method for amplifying a target HSV DNA optionally present in a sample, comprising the steps of:
   A) incubating the sample in a reaction mixture comprising an amplification buffer with:
      1) one or more restriction enzymes that cleave the target HSV DNA at a selected restriction site, said restriction enzyme creating a defined 3'-end on one of the target HSV DNA strands;
      2) a promoter-primer, said promoter-primer having a 5' region comprising a nucleotide sequence of a promoter recognized by a DNA-dependent RNA polymerase and a 3' region complementary to the defined 3' end of the target HSV DNA strand of (1) above and comprising the second isolated oligonucleotide of the pair of isolated oligonucleotides of claim 1; and
      3) a second primer comprising the 5'-end of the target sequence and the first isolated oligonucleotide of the pair of isolated oligonucleotides of claim 1;
   B) maintaining the reaction mixture of (A) above under the conditions whereby digestion by the restriction enzyme occurs, in the presence of appropriate nucleoside triphosphates;
   C) subjecting the reaction mixture of (B) above to a heat treatment at a temperature and time sufficient to inactivate the restriction enzyme(s) and optionally rendering double stranded HSV DNA at least partially single stranded;
   D) adding the following reagents to the reaction mixture of (C) above:
      1) an enzyme having RNA dependent DNA polymerase activity;
      2) an enzyme having DNA dependent DNA polymerase activity;
      3) an enzyme having RNase H activity; and
      4) an enzyme having DNA dependent RNA polymerase activity; and
   E) maintaining the reaction mixture of (D) above under conditions whereby amplification of any target HSV nucleic acid present in the sample can occur.

4. The method according to claim 3, wherein the HSV nucleic acid is double stranded HSV DNA.

5. The method according to claim 3, wherein the HSV DNA is single stranded and the promoter-primer is combined with a restriction primer, and wherein the combined promoter-primer and restriction primer comprise a nucleotide sequence that is complementary to a region that includes a selected restriction site on the target single stranded HSV DNA and a nucleotide sequence of a promoter recognized by a DNA-dependent RNA polymerase.

6. The method according to claim 3, wherein the RNA dependent DNA polymerase activity and the DNA dependent DNA polymerase activity are provided by a reverse transcriptase.

7. The method according to claim 3, wherein the RNA dependent DNA polymerase activity, the DNA dependent DNA activity, and the RNase H activity are provided by a reverse transcriptase.

8. The method according to claim 3, wherein the incubating of step (A) is carried out at a temperature from about 35° C. to about 45° C.

9. The method according to claim 3, wherein the heat treatment of step (C) is carried out at a temperature from about 92° C. to about 98° C.

10. The method according to claim 3, wherein the restriction enzyme cuts the HSV DNA at a site that is conserved among the different genotypes of HSV.

11. A method for detecting HSV nucleic acid in a sample comprising:
   (a) subjecting the sample to a nucleic acid amplification reaction using the pair of isolated oligonucleotides of claim 1 under conditions whereby amplification of HSV nucleic acid can occur; and
   (b) detecting amplified HSV nucleic acid in the sample.

12. The method according to claim 11, wherein the amplification technique used is a transcription based amplification technique and the first isolated oligonucleotide comprises a promoter nucleotide sequence recognized by a DNA dependent RNA polymerase.

13. The method according to claim 11, wherein detecting the amplified HSV nucleic acid in a sample comprises:
contacting the amplified HSV nucleic acid in the sample with an isolated oligonucleotide under conditions whereby hybridization can occur, said isolated oligonucleotide being 10-50 nucleotides in length and comprising at least 20 contiguous nucleotides of a nucleotide sequence consisting of: 5'-GAAAAAGTACATCG-GCGTCATCT-3' (SEQ ID NO:3), or its full complement; and
detecting hybridization between the amplified HSV nucleic acid and said isolated oligonucleotide.

14. The method according to claim 11, wherein detecting the amplified HSV nucleic acid in a sample comprises:
contacting the amplified HSV nucleic acid in the sample with an isolated oligonucleotide under conditions whereby hybridization can occur, said isolated oligonucleotide being 10-50 nucleotides in length and comprising at least 10 contiguous nucleotides of a nucleotide sequence consisting of: 5'-GTCATCTACGGGGG-TAAG-3' (SEQ ID NO:4), or its full complement; and
detecting hybridization between the amplified HSV nucleic acid and said isolated oligonucleotide.

15. The method according to claim 11, wherein detecting the amplified HSV nucleic acid in a sample comprises:
contacting the amplified HSV nucleic acid in the sample with the isolated oligonucleotide under conditions whereby hybridization can occur, said isolated oligonucleotide being 10-50 nucleotides in length and comprising at least 10 contiguous nucleotides of a nucleotide sequence consisting of: 5'GTCATCT-GCGGGGGCAAG-3' (SEQ ID NO:5), or its full complement; and
detecting hybridization between the amplified HSV nucleic acid and said isolated oligonucleotide.

16. The method according to claim 11, wherein detecting any amplified HSV nucleic acid in a sample comprises:
contacting the amplified HSV nucleic acid in the sample with a pair of isolated oligonucleotides under conditions whereby hybridization can occur, said pair of isolated oligonucleotides comprising:
i) an isolated oligonucleotide, being 10-50 nucleotides in length and comprising at least 10 contiguous nucleotides of a nucleotide sequence consisting of: 5'-GTCATCTACGGGGGTAAG-3' (SEQ ID NO:4), or its full complement; and
ii) an isolated oligonucleotide, being 10-50 nucleotides in length and comprising at least 10 contiguous nucleotides of a nucleotide sequence consisting of: 5'-GTCATCTGCGGGGGCAAG-3' (SEQ ID NO:5), or its full complement; and
detecting hybridization between the amplified HSV nucleic acid and said isolated oligonucleotides.

17. A method for detecting HSV nucleic acid in a sample comprising:
(a) amplifying the HSV nucleic acid in the sample according to claim 3;
(b) contacting the amplified HSV nucleic acid in the sample with an isolated oligonucleotide under conditions whereby hybridization can occur, said isolated oligonucleotide being 10-50 nucleotides in length and comprising at least 20 contiguous nucleotides of a nucleotide sequence consisting of: 5'-GAAAAAGTA-CATCGGCGTCATCT-3' (SEQ ID NO:3), or its full complement; and
(c) detecting hybridization between the amplified HSV nucleic acid and said isolated oligonucleotide.

18. A method for detecting HSV type 1 nucleic acid in a sample, comprising:
(a) amplifying the HSV nucleic acid in the sample according to claim 3;
(b) contacting the amplified HSV nucleic acid in the sample with an isolated oligonucleotide under conditions whereby hybridization can occur, said isolated oligonucleotide being 10-50 nucleotides in length and comprising at least 10 contiguous nucleotides of a nucleotide sequence consisting of: 5'-GTCATC-TACGGGGGTAAG-3' (SEQ ID NO:4), or its full complement; and
(c) detecting hybridization between the amplified HSV nucleic acid and said isolated oligonucleotide.

19. A method for detecting HSV type 2 nucleic acid in a sample, comprising:
(a) amplifying the HSV nucleic acid in the sample according to claim 3;
(b) contacting the amplified HSV nucleic acid in the sample with an isolated oligonucleotide under conditions whereby hybridization can occur, said isolated oligonucleotide being 10-50 nucleotides in length and comprising at least 10 contiguous nucleotides of a nucleotide sequence consisting of: 5'GTCATCT-GCGGGGGCAAG-3' (SEQ ID NO:5), or its full complement; and
(c) detecting hybridization between the amplified HSV nucleic acid and said isolated oligonucleotide.

20. A method for detecting HSV nucleic acid in a sample, comprising:
(a) amplifying the HSV nucleic acid in the sample according to claim 3;
(b) contacting the amplified HSV nucleic acid in the sample with a pair of isolated oligonucleotides under conditions whereby hybridization can occur, said pair of isolated oligonucleotides comprising:
i) an isolated oligonucleotide, being 10-50 nucleotides in length and comprising at least 10 contiguous nucleotides of a nucleotide sequence consisting of: 5'-GTCATCTACGGGGGTAAG-3' (SEQ ID NO:4), or its full complement; and
ii) an isolated oligonucleotide, being 10-50 nucleotides in length and comprising at least 10 contiguous nucleotides of a nucleotide sequence consisting of: 5'-GTCATCTGCGGGGGCAAG-3' (SEQ ID NO:5), or its full complement; and
(c) detecting hybridization between the amplified HSV nucleic acid and said isolated oligonucleotides.

21. A method for detecting HSV nucleic acid in a sample, comprising:
(a) amplifying the HSV nucleic acid in the sample according to claim 3;
(b) contacting the sample with the pair of isolated oligonucleotides of claim 1, under conditions whereby hybridization can occur; and
(c) detecting hybridization between the amplified HSV nucleic acid and said isolated oligonucleotides.

22. A kit for detecting HSV nucleic acid in a sample comprising:
(a) a pair of isolated oligonucleotides according to claim 1;
(b) an isolated oligonucleotide, being 20-35 nucleotides in length and comprising at least the nucleotide sequence: 5'-GAAAAAGTACATCGGCGTCATCT-3' (SEQ ID NO:3), or the full complement of the nucleotide sequence of SEQ ID NO:3, provided with a detectable label;
(c) suitable amplification reagents; and
(d) optionally at least one restriction enzyme.

23. A kit for detecting HSV nucleic acid in a sample, wherein the kit comprises a pair of primers, primer (a) and primer (b), wherein primer (a) comprises an RNA polymerase promoter sequence and a hybridizing sequence comprising the second isolated oligonucleotide of claim 1, and primer (b) comprises the first isolated oligonucleotide of claim 1.

24. The kit according to claim 23, further comprising an isolated oligonucleotide comprising a nucleotide sequence that hybridizes to the region of the HSV DNA that is amplified using primer (a) and primer (b).

25. The kit according to claim 24, wherein the amplification reagents are suitable for a transcription based amplification technique.

26. A kit for detecting HSV nucleic acid in a sample comprising:
(a) a pair of isolated oligonucleotides according to claim 1,
(b) an isolated oligonucleotide, being 10-50 nucleotides in length and comprising at least 10 contiguous nucleotides of a nucleotide sequence consisting of: 5'-GTCATCTACGGGGGTAAG-3' (SEQ ID NO:4), or its full complement, provided with a detectable label,
(c) suitable amplification reagents, and
(d) optionally at least one restriction enzyme.

27. A kit for detecting HSV nucleic acid in a sample comprising:
(a) a pair of isolated oligonucleotides according to claim 1,
(b) an isolated oligonucleotide, being 10-50 nucleotides in length and comprising at least 10 contiguous nucleotides of a nucleotide sequence consisting of: 5'GTCATCTGCGGGGGCAAG-3' (SEQ ID NO:5), or its full complement, provided with a detectable label,
(c) suitable amplification reagents, and
(d) optionally at least one restriction enzyme.

28. A kit for detecting HSV nucleic acid in a sample comprising:
(a) a pair of isolated oligonucleotides according to claim 1,
(b) a pair of isolated oligonucleotides comprising:
    i) an isolated oligonucleotide, being 10-50 nucleotides in length and comprising at least 10 contiguous nucleotides of a nucleotide sequence consisting of: 5'-GTCATCTACGGGGGTAAG-3' (SEQ ID NO:4), or its full complement; and
    ii) an isolated oligonucleotide, being 10-50 nucleotides in length and comprising at least 10 contiguous nucleotides of a nucleotide sequence consisting of: 5'-GTCATCTGCGGGGGCAAG-3' (SEQ ID NO:5), or its full complement, provided with a detectable label,
(c) suitable amplification reagents, and
(d) optionally at least one restriction enzyme.

* * * * *

UNITED STATES PATENT AND TRADEMARK OFFICE
CERTIFICATE OF CORRECTION

PATENT NO. : 8,298,761 B2  Page 1 of 1
APPLICATION NO. : 11/791135
DATED : October 30, 2012
INVENTOR(S) : Deiman et al.

It is certified that error appears in the above-identified patent and that said Letters Patent is hereby corrected as shown below:

In the Claims:
Column 19, Claim 1, Lines 29 and 30:
  Please correct "oligonucleotide, being 20 nucleotides in length and comprising the"
    to read -- oligonucleotide, consisting of the --

Column 23, Claim 25, Line 16:
  Please correct "according to claim 24," to read -- according to claim 22, --

Signed and Sealed this
Twenty-ninth Day of October, 2013

Teresa Stanek Rea
*Deputy Director of the United States Patent and Trademark Office*

```
                        SEQUENCE LISTING

<160> NUMBER OF SEQ ID NOS: 18

<210> SEQ ID NO 1
<211> LENGTH: 20
<212> TYPE: DNA
<213> ORGANISM: herpes simplex virus

<400> SEQUENCE: 1
acgttcacca agctgctgct                                                    20

<210> SEQ ID NO 2
<211> LENGTH: 20
<212> TYPE: DNA
<213> ORGANISM: herpes simplex virus

<400> SEQUENCE: 2
ccagggccct ggaggtgcgg                                                    20

<210> SEQ ID NO 3
<211> LENGTH: 23
<212> TYPE: DNA
<213> ORGANISM: herpes simplex virus

<400> SEQUENCE: 3
gaaaaagtac atcggcgtca tct                                                23

<210> SEQ ID NO 4
<211> LENGTH: 18
<212> TYPE: DNA
<213> ORGANISM: herpes simplex virus

<400> SEQUENCE: 4
gtcatctacg ggggtaag                                                      18

<210> SEQ ID NO 5
<211> LENGTH: 18
```

```
-continued

<212> TYPE: DNA
<213> ORGANISM: herpes simplex virus

<400> SEQUENCE: 5
gtcatctgcg ggggcaag                                                 18

<210> SEQ ID NO 6
<211> LENGTH: 18
<212> TYPE: DNA
<213> ORGANISM: herpes simplex virus

<400> SEQUENCE: 6
gtcatctacg ggggtaag                                                 18

<210> SEQ ID NO 7
<211> LENGTH: 18
<212> TYPE: DNA
<213> ORGANISM: herpes simplex virus

<400> SEQUENCE: 7
gtcatctgcg ggggcaag                                                 18

<210> SEQ ID NO 8
<211> LENGTH: 20
<212> TYPE: DNA
<213> ORGANISM: Artificial
<220> FEATURE:
<223> OTHER INFORMATION: DNA-dependent RNA polymerase promoter primer

<400> SEQUENCE: 8
ccagggccct ggaggtgcgg                                               20

<210> SEQ ID NO 9
<211> LENGTH: 20
<212> TYPE: DNA
<213> ORGANISM: Artificial
<220> FEATURE:
<223> OTHER INFORMATION: opposite polarity promoter-primer

<400> SEQUENCE: 9
acgttcacca agctgctgct                                               20

<210> SEQ ID NO 10
<211> LENGTH: 51
<212> TYPE: DNA
<213> ORGANISM: Artificial
<220> FEATURE:
<223> OTHER INFORMATION: HSV_pol P3.1 primer/probe

<400> SEQUENCE: 10
aattctaata cgactcacta tagggccctg gtcgacctgc tgttttacga c            51

<210> SEQ ID NO 11
<211> LENGTH: 51
<212> TYPE: DNA
<213> ORGANISM: Artificial
<220> FEATURE:
<223> OTHER INFORMATION: HSV_pol P3.2  primer/probe

<400> SEQUENCE: 11
aattctaata cgactcacta tagggagacc tgctgtttta cgacgatacc g            51

<210> SEQ ID NO 12
<211> LENGTH: 20
<212> TYPE: DNA
<213> ORGANISM: Artificial
```

```
<220> FEATURE:
<223> OTHER INFORMATION: HSV pol P4.1 primer/probe

<400> SEQUENCE: 12
tctgctcagt tcggcggtga                                               20

<210> SEQ ID NO 13
<211> LENGTH: 48
<212> TYPE: DNA
<213> ORGANISM: Artificial
<220> FEATURE:
<223> OTHER INFORMATION: HSV_pol P1.1 primer/probe

<400> SEQUENCE: 13
aattctaata cgactcacta tagggagacc agggccctgg aggtgcgg                48

<210> SEQ ID NO 14
<211> LENGTH: 21
<212> TYPE: DNA
<213> ORGANISM: Artificial
<220> FEATURE:
<223> OTHER INFORMATION: HSV_pol P2.1 primer/probe

<400> SEQUENCE: 14
gggcgacaag atggcgagcc a                                             21

<210> SEQ ID NO 15
<211> LENGTH: 31
<212> TYPE: DNA
<213> ORGANISM: Artificial
<220> FEATURE:
<223> OTHER INFORMATION: OTMB8515 primer/probe

<400> SEQUENCE: 15
cgatcgcccc gaacgcctgc agtcccgatc g                                  31

<210> SEQ ID NO 16
<211> LENGTH: 34
<212> TYPE: DNA
<213> ORGANISM: Artificial
<220> FEATURE:
<223> OTHER INFORMATION: OTMB8516 primer/probe

<400> SEQUENCE: 16
cgatcgaaaa gtacatcggc gtcatctacg atcg                               34

<210> SEQ ID NO 17
<211> LENGTH: 32
<212> TYPE: DNA
<213> ORGANISM: Artificial
<220> FEATURE:
<223> OTHER INFORMATION: OTMB8547 primer/probe
<220> FEATURE:
<221> NAME/KEY: misc_feature
<222> LOCATION: (1)..(25)
<223> OTHER INFORMATION: n = inosine
<220> FEATURE:
<221> NAME/KEY: modified_base
<222> LOCATION: (3)..(3)
<223> OTHER INFORMATION: methoxy adenine (A)
<220> FEATURE:
<221> NAME/KEY: modified_base
<222> LOCATION: (15)..(15)
<223> OTHER INFORMATION: methoxy adenine (A)
<220> FEATURE:
<221> NAME/KEY: modified_base
<222> LOCATION: (26)..(28)
<223> OTHER INFORMATION: methoxy guanine (G)
<220> FEATURE:
<221> NAME/KEY: modified_base
```

-continued

```
<222> LOCATION: (31)..(31)
<223> OTHER INFORMATION: methoxy adenine (A)
<220> FEATURE:
<221> NAME/KEY: modified_base
<222> LOCATION: (32)..(32)
<223> OTHER INFORMATION: methoxy guanine (G)

<400> SEQUENCE: 17
ctatcccgtc atctacggng gtaaggggat ag                              32

<210> SEQ ID NO 18
<211> LENGTH: 30
<212> TYPE: DNA
<213> ORGANISM: Artificial
<220> FEATURE:
<223> OTHER INFORMATION: OTMB8562 primer/probe

<400> SEQUENCE: 18
cgatcggtca tctgcggggg caagcgatcg                                 30
```